US009184034B2

(12) United States Patent
Eaton

(10) Patent No.: US 9,184,034 B2
(45) Date of Patent: Nov. 10, 2015

(54) PHOTOMULTIPLIER TUBE WITH EXTENDED DYNAMIC RANGE

(71) Applicant: KLA-Tencor Corporation, Milpitas, CA (US)

(72) Inventor: Michael Eaton, Menlo Park, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 62 days.

(21) Appl. No.: 13/788,945

(22) Filed: Mar. 7, 2013

(65) Prior Publication Data

US 2013/0242291 A1    Sep. 19, 2013

Related U.S. Application Data

(60) Provisional application No. 61/612,830, filed on Mar. 19, 2012.

(51) Int. Cl.
| | |
|---|---|
| *G01N 21/00* | (2006.01) |
| *H01J 43/28* | (2006.01) |
| *G01N 21/88* | (2006.01) |
| *G01N 21/95* | (2006.01) |

(52) U.S. Cl.
CPC ............... *H01J 43/28* (2013.01); *G01N 21/88* (2013.01); *G01N 21/8806* (2013.01); *G01N 21/9501* (2013.01); *G01N 2021/8822* (2013.01)

(58) Field of Classification Search
CPC .......... H01J 43/30; H01J 43/04; H01J 43/06; H01J 43/18; H01J 43/22; G01N 2021/8822; G01N 21/9501; G01N 21/47; G01N 21/88

USPC .............. 356/237.1–237.5; 250/207, 214 VT; 313/532–536, 103, 105 R

See application file for complete search history.

(56) References Cited

U.S. PATENT DOCUMENTS

| | | | | | |
|---|---|---|---|---|---|
| 3,695,761 | A | * | 10/1972 | Crosswy et al. ................. | 356/28 |
| 4,649,269 | A | * | 3/1987 | Persyk .......................... | 250/207 |
| 4,691,160 | A | * | 9/1987 | Ino .............................. | 324/71.3 |
| 5,043,628 | A | * | 8/1991 | Boutot et al. .................. | 313/532 |
| 5,598,061 | A | * | 1/1997 | Nakamura et al. ............. | 313/532 |
| 5,689,152 | A |   | 11/1997 | Boutot | |
| 5,914,561 | A | * | 6/1999 | Venkatarao et al. ........... | 313/533 |
| 6,373,067 | B1 | * | 4/2002 | Shimomura ................... | 250/397 |

(Continued)

FOREIGN PATENT DOCUMENTS

| | | |
|---|---|---|
| RU | 87801 U1 | 10/2009 |
| SU | 273887 A1 | 7/1970 |
| SU | 368718 A1 | 1/1973 |
| SU | 851549 A1 | 7/1981 |
| SU | 966788 A1 | 10/1982 |

*Primary Examiner* — Hoa Pham
(74) *Attorney, Agent, or Firm* — Suiter Swantz pc llo

(57) ABSTRACT

The disclosure is directed to a photomultiplier tube with extended dynamic range. According to various embodiments, a repulsive electric field is introduced between a photocathode and a plurality of dynodes in order to repel or block low-energy electrons from reaching and being multiplied by the dynodes. As a result, time intervals between current peaks and drops may be decreased because the photomultiplier current will be primarily affected by high-energy electrons emitted by the photocathode in response to incident illumination versus low-energy electrons, some of which may result from dangling bonds or slow surface states after illumination no longer impinges the photocathode. Dynamic range and optical responsiveness of the photomultiplier tube are increased accordingly.

25 Claims, 4 Drawing Sheets

(56) References Cited

U.S. PATENT DOCUMENTS

| | | | |
|---|---|---|---|
| 6,462,324 B1* | 10/2002 | Wright et al. | 250/207 |
| 6,927,538 B2* | 8/2005 | Ishizu et al. | 313/533 |
| 6,946,792 B2* | 9/2005 | Kimura et al. | 313/532 |
| 7,777,875 B2* | 8/2010 | Wolters et al. | 356/237.2 |
| 2003/0201720 A1* | 10/2003 | Ooae et al. | 315/32 |
| 2004/0016867 A1* | 1/2004 | Milshtein et al. | 250/207 |
| 2010/0187413 A1* | 7/2010 | DiFoggio et al. | 250/269.1 |

\* cited by examiner

PHOTOMULTIPLIER TUBE WITH EXTENDED DYNAMIC RANGE

PRIORITY

The present application claims priority to U.S. Provisional Application Ser. No. 61/612,830, entitled PMT WITH EXTENDED DYNAMIC RANGE, By Michael Eaton, filed Mar. 19, 2012, which is currently co-pending, or is an application of which a currently co-pending application is entitled to the benefit of the filing date.

TECHNICAL FIELD

The present disclosure generally relates to the field of photomultiplier tubes and more particularly to systems and methods of extending dynamic range of a photomultiplier tube.

BACKGROUND

Photomultiplier tubes (PMTs) are photo-detectors capable of detecting low intensity illumination. As such, PMTs are used in many low intensity applications including, but not limited to, cell imaging, biodiagnostic instrumentation, semiconductor wafer inspection, particle counting, nuclear medicine, radiation detection, quantum cryptography, and low light imaging (e.g. security cameras or light detection and ranging (LIDAR) systems). PMTs have been used to detect low-energy photons with wavelengths from infrared (IR) range to the ultraviolet (UV) range as well as high-energy photons such as X-rays or gamma rays.

A PMT generally includes a photocathode, a plurality of dynodes (making up an electron multiplier), and an anode. When illumination impinges upon an entrance window of a PMT, photons from the incident illumination strike a surface of the photocathode and are converted into photoelectrons, which are then accelerated by a high electric field through a path delineated by the plurality of dynodes. The photoelectrons are multiplied by secondary electron emissions from the dynodes before being collected by the anode. The electrons received by the anode produce a current associated with the intensity of the incident illumination.

Depending on the configuration of a PMT and the voltages applied to the electrodes, the PMT can serve as a detector operable in a single-photon counting mode as well as in an analog or proportional mode. In addition, PMTs generally have a large sensing area, are highly responsive, and may have high signal-to-noise ratio (SNR). In some applications, PMTs are used to detect incident illumination ranging from a single photon (less than an attowatt) up to billions of photons (picowatts to nanowatts) per second.

However, existing PMTs do not meet dynamic range requirements demanded by some state of the art and emerging applications. The dynamic range is limited by the slow decay of persisting current that results from an intensity peak (i.e. the sudden rise in current due to incident illumination). As a result, existing PMTs also have inadequate sensitivity (i.e. optical responsiveness) to incident illumination that is very quickly and dynamically changing. For example, it may be difficult to detect a low intensity peak following a very high intensity peak without enough time separation for persisting current from the first (very high intensity) peak to sufficiently decay.

SUMMARY

The present disclosure is directed to a photomultiplier tube that cures one or more deficiencies in the current state of the art.

In one aspect, the disclosure is directed to a photomultiplier tube, including: a photocathode configured to emit electrons in response to incident illumination; a plurality of dynodes configured to multiply electrons received from the photocathode; an anode configured to receive electrons multiplied by the plurality of dynodes; and a control grid configured to prevent a portion of the electrons (i.e. low-energy electrons) emitted by the photocathode from being received by the plurality of dynodes.

In another aspect, the disclosure is directed to an inspection system including at least one illumination source and at least one detector, where the detector includes the photomultiplier tube. The illumination source is configured to illuminate a sample with illumination directed along an illumination path to at least a portion of the sample surface. The detector is configured to receive illumination scattered or reflected from the sample along a collection path to the detector. At least one computing system in communication with the detector is configured to determine information associated with at least one defect of the sample based upon the illumination received by the detector from the sample.

In yet another aspect, the disclosure is directed to a method of extending dynamic range of a photomultiplier tube, including at least the following steps: providing a photocathode configured to emit electrons in response to incident illumination; providing a plurality of dynodes configured to multiply electrons received from the photocathode; providing an anode configured to receive electrons multiplied by the plurality of dynodes; and introducing a repulsive electric field to prevent a portion of the electrons emitted by the photocathode from being received by the plurality of dynodes. The method may be manifested by an embodiment of the photomultiplier tube and/or inspection system described herein. In some embodiments, however, one or more steps of the method may be accomplished by additional or alternative means known to the art. Accordingly, the method should be broadly construed to encompass any appropriate means for carrying out the foregoing steps and the steps described in further detail below.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Figure 1A:
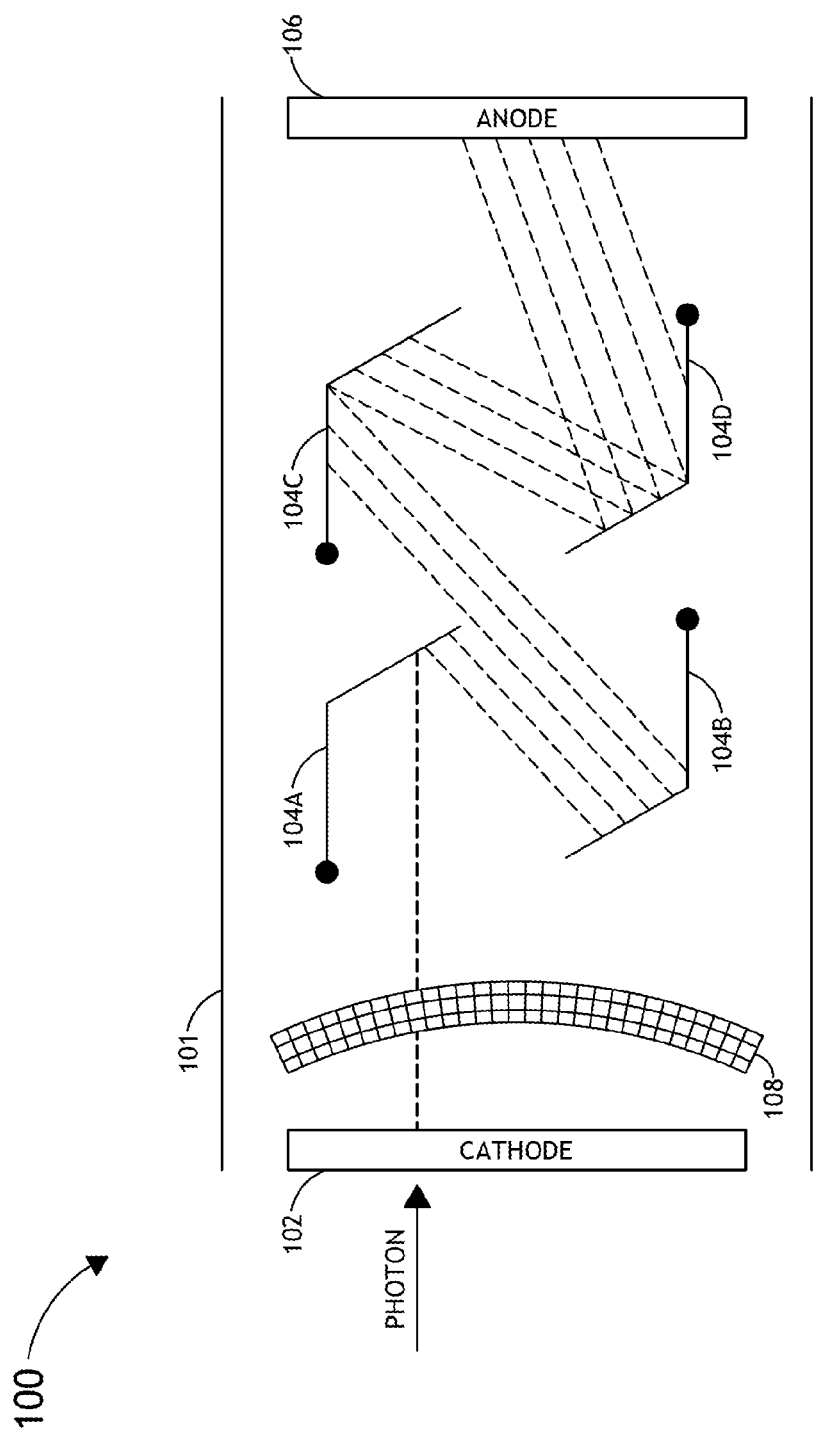
FIG. 1A is a block diagram illustrating a photomultiplier tube, in accordance with an embodiment of this disclosure.
Figure 1B:
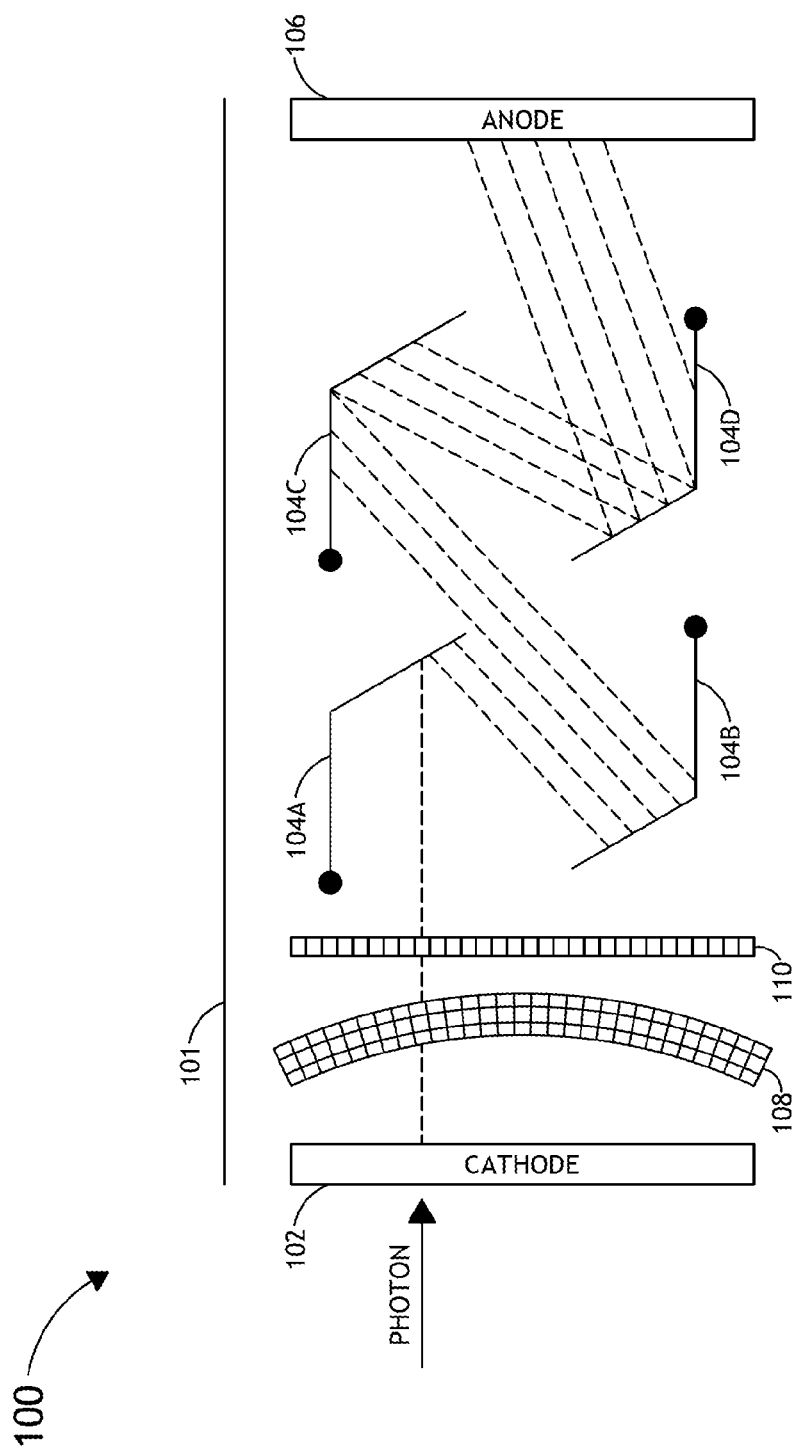
FIG. 1B is a block diagram illustrating the photomultiplier tube, in accordance with another embodiment of this disclosure.

FIGS. 1A and 1B illustrate embodiments of a photomultiplier tube (PMT) 100 in accordance with this disclosure. According to various embodiments, the PMT 100 includes at least a photocathode 102, a plurality of dynodes 104, and an anode 106. When illumination impinges upon an entrance window of the PMT 100, photons from the incident illumination strike a surface of the photocathode 102. The photocathode 102 is configured to emit electrons in response to the incident illumination, which are then accelerated through a multiplier tube 101 including the plurality of dynodes 104. The dynodes 104 are configured to multiply the number of electrons flowing through the multiplier tube 101 via secondary electron emissions from electron collisions with one or more of the dynodes 104. For example, as electrons from the photocathode 102 collide with a first dynode 104A they are multiplied and may be directed to a second dynode 104B which further multiplies the electrons and so on. The anode 106 is configured to receive the multiplied electrons, and a spike in current (i.e. an intensity peak) can be detected accordingly. As a result of the multiplication, the intensity peak may exhibit a proportional relationship with the intensity of the incident illumination.

In some photomultiplier tubes, persisting current is often detected after an intensity peak. The persisting current typically decays according to a long time constant or a series of increasingly longer time constants upon cessation of the intensity peak. The slowed decay may be caused by low-energy surface states (e.g. dangling bonds) existing at a surface of the photocathode 102. For example, some electrons resulting from the incident illumination may have insufficient energy for release into the multiplier vacuum tube 101 immediately following the incident illumination. Instead these low-energy electrons may be captured in a low-energy surface state. After illumination of the photocathode 102 ceases, some of the captured electrons may be liberated from a surface state by energy gained from a source other than incident illumination, such as thermionic excitation. The post-illumination emissions may result in slow decay of current following an initial drop from the intensity peak associated with the incident illumination. For example, incident illumination may cause an intensity peak of approximately 100 dB above the noise floor, followed by a 40 to 50 dB drop (after illumination is extinguished) and slow (long time constant) decay of current thereafter. As the foregoing example illustrates, the dynamic range may be substantially limited by the post-illumination electron emissions (e.g. less than half of the total range). It is noted herein that the foregoing exemplary values are included for illustrative purposes and are not intended to limit the present disclosure in any way.

To mitigate persisting current from post-illumination emissions of low-energy electrons, as discussed above, the PMT 100 includes a control grid 108 configured to prevent at least a portion of low-energy electrons from reaching the dynodes 104 and contributing to the PMT current. The control grid 108 may include any means configured to provide a repulsive electric field between the photocathode 102 and a first dynode 104A of the plurality of dynodes 104. Accordingly, electrons released by the photocathode 102 with kinetic energy levels below a threshold are repelled by the electric field so that the low-energy electrons are not accelerated through the dynodes 104 along the multiplier tube 101. In some embodiments, the construction of the PMT 100 follows the configuration of a conventional vacuum triode, with the first dynode 104A replacing the plate electrode of the conventional vacuum triode. However, the control grid 108 of the PMT 100 serves the purpose of introducing a repulsive electric field to prevent low-energy electrons emitted by the photocathode 102 from affecting the PMT anode current.

The control grid 108 may include at least one conductor, such as a fine wire mesh, disposed near the photocathode 102. In some embodiments, the control grid 108 is oriented substantially parallel to the photocathode 102. The control grid 108 may be configured to carry a selected electric potential that is negative to that of the photocathode 102 across at least one conductive surface to generate the electric field for repelling low-energy (post-illumination) electron emissions by the photocathode 102. However, the selected electric potential is sufficiently small to allow high-energy electrons (i.e. those resulting immediately from incident illumination) to traverse the resulting field and accelerate through the dynodes 104 to the anode 106. As a result, electrons emitted by the photocathode 102 due to thermal excitation of surface states are prevented from contributing the PMT current. Dynamic range is thereby increased because intensity peaks from incident illumination are followed by rapidly decaying current (i.e. sudden rise in current followed by sudden drop to the noise floor).

In some embodiments, the selected electric potential enabling photoelectrons liberated by incident illumination may be determined utilizing the equation $E_k = h\nu - w$, where electrons having energy $E_k$ are enabled to traverse the electric field introduced by the control grid 108, h is Planck's constant, v is the frequency of incident illumination, and w is the work function of metal. For example, if the work function of a cesium telluride photocathode 102 is approximately 1.5 eV, the high-energy or primary electrons emitted from the first monolayer may have approximate kinetic energy $E_k = 3$ eV when incident illumination with a wavelength of approximately 266 nm is applied. Accordingly, the control grid 108 may operate at an electric potential of approximately −0.5 to −1V relative to the photocathode 102 to avoid repelling primary electrons. However, the field resulting from the control grid 108 when added to the field resulting from the first dynode 104A provides a net repulsive force towards the surface of the cathode 102 to repel low-energy electrons resulting from the release from low-energy surface states. The foregoing example is provided for illustrative purposes only and is not intended to limit the present disclosure in any way. It will be appreciated that the selected electric potential applied to the control grid 108 will vary according to the implementation at hand.

In some embodiments, illustrated in FIG. 1B, the PMT 100 may further include an accelerating grid 110 disposed between the control grid 108 and the first dynode 104A. The accelerating grid 110 may be configured to provide a low field of acceleration to move primary electrons beyond the control grid 108 to the first dynode 104A. In some embodiments, the accelerating grid 110 is further configured to shield the control grid 108 from the high electric potential of the first dynode 104A. For example, the accelerating grid 110 may operate at lower electric potential (e.g. approximately +15V) than the high electric potential (e.g. approximately +50 to +100V) of the first dynode 104A. In some embodiments, the conductive surface of the control grid 108 is further shaped to enable electron focusing through the acceleration field of the accelerating grid 110 and/or the dynodes 104. For example, the control grid 108 may include a fine wire mesh configured with a selected curvature to focus electrons traversing the electric field introduced by the control grid 108.

Figure 2:
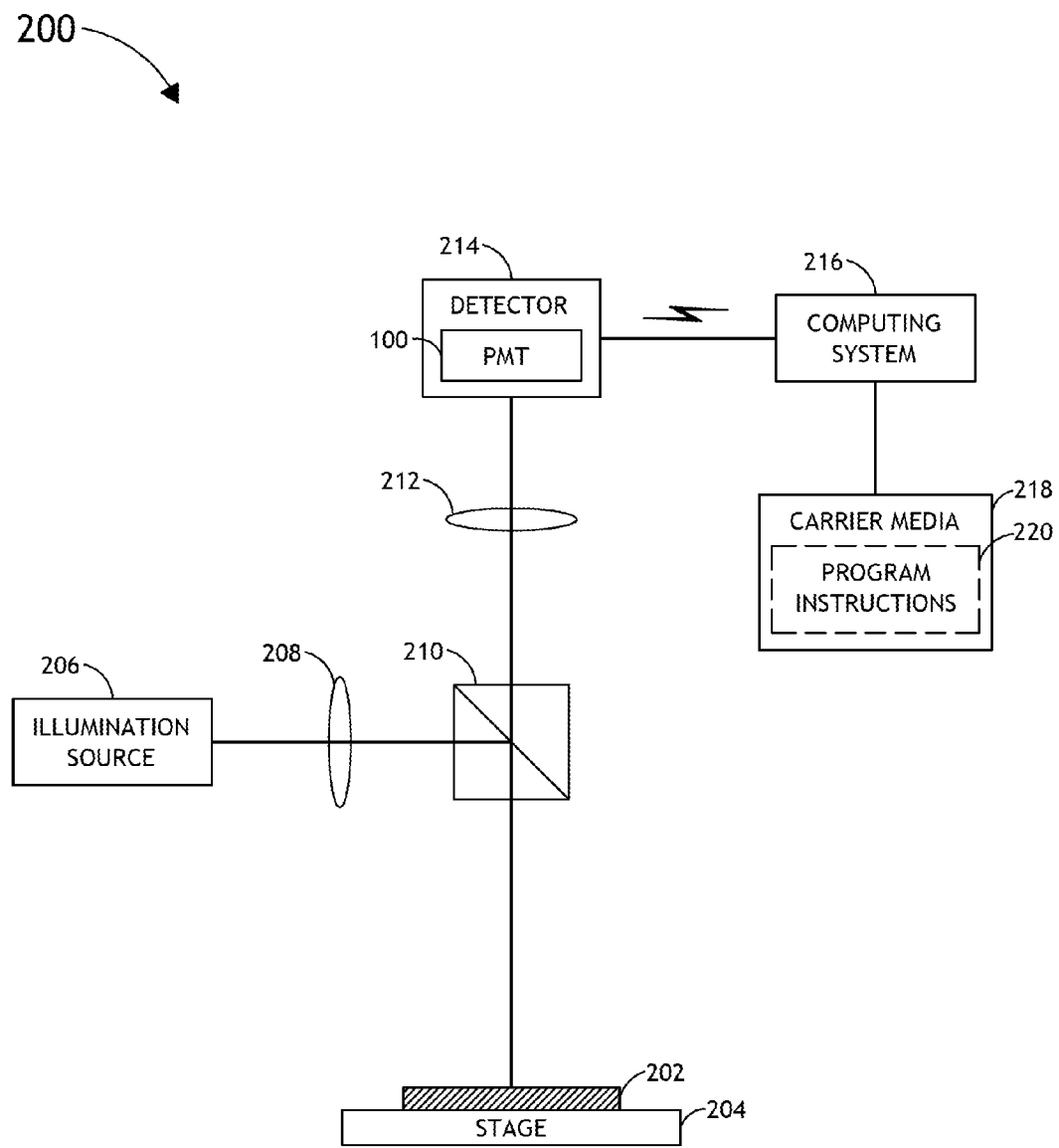
FIG. 2 is a block diagram illustrating an inspection system, in accordance with an embodiment of this disclosure.

FIG. 2 illustrates an inspection system 200 incorporating the PMT 100, in accordance with an embodiment of this disclosure. The inspection system 200 may include any system utilizing a PMT to detect illumination reflected, scattered, and/or radiated from the surface of a sample 202 (e.g. semiconductor wafer, mask, or non-semiconductor sample). For example, the inspection system 200 may include, but is not limited to a darkfield inspection or imaging system.

The inspection system 200 may include a stage 204 configured to support the sample 202. In some embodiments, the stage 204 is further configured to actuate the sample 202 to a selected position or orientation. For example, the stage 204 may include or may be mechanically coupled to at least one actuator, such as a motor or servo, configured to translate or rotate the sample 202 for positioning, focusing, and/or scanning in accordance with a selected inspection or imaging algorithm, several of which are known to the art.

The system 200 may further include an illumination source 206 configured to provide illumination along an illumination path delineated by one or more illumination optics 208 to a surface of the sample 202. In some embodiments, the illumination path further includes a beam splitter 210 configured to direct at least a portion of the illumination to the surface of the sample 202 and illumination reflected, scattered, or radiated from the surface of the sample 202 along a collection path delineated by one or more collection optics 212 to a detector 214 including the PMT 100 (as described above). As used herein, the terms illumination optics and collection optics include any combination of optical elements such as, but not limited to, focusing lenses, diffractive elements, polarizing elements, optical fibers, and the like.

The inspection system 200 may further include at least one computing system 216 communicatively coupled to the detector 214. The computing system 216 may include, but is not limited to, a personal computing system, mainframe computing system, workstation, image computer, parallel processor, or any processing device known in the art. In general, the term "computing system" may be broadly defined to encompass any device having one or more processors configured to execute program instructions 220 from at least one carrier medium 218.

The computing system 216 may be configured to receive information (e.g. image frames, pixels, intensity measurements) associated with illumination collected by the detector 214. The computing system 216 may be further configured to carry out various inspection, imaging, and/or sample analysis algorithms known to the art utilizing the collected information. For example, the computing system 216 may be configured to locate one or more defects of the sample 202 and/or generate review images associated with the one or more defects. In some embodiments, the computing system 216 may be further configured to characterize the one or more defects (e.g. brightfield or darkfield defect, spatial property of defect). In some embodiments, the computing system 216 may be further configured to execute or control execution of various steps or functions described herein. For example, the computing system 216 may be configured to control: the PMT 100 (e.g. voltages applied to various terminals), the illumination source 206, and/or the one or more stage actuators.

Figure 3:
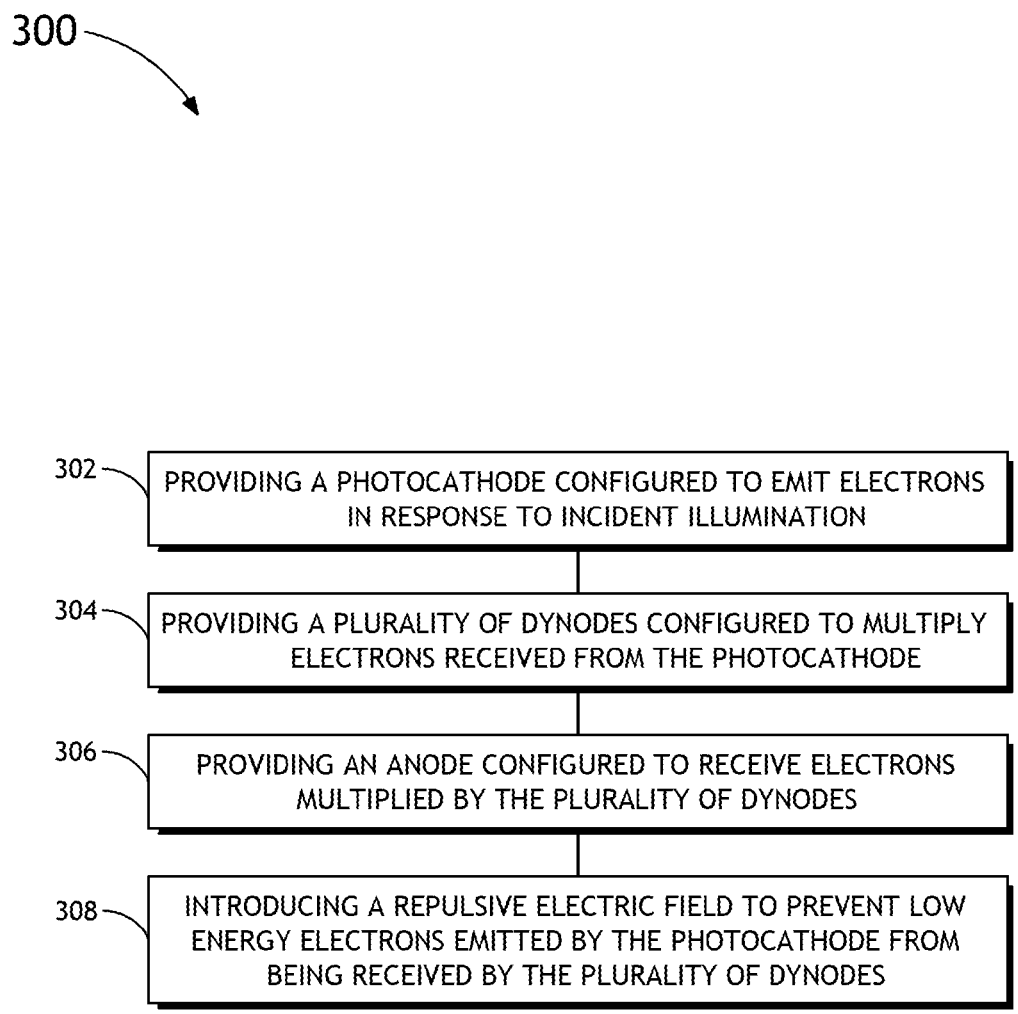
FIG. 3 is a flow diagram illustrating a method of extending dynamic range of a photomultiplier tube, in accordance with an embodiment of this disclosure.

FIG. 3 is a flow diagram illustrating a method 300 of providing a PMT 100 with extended dynamic range. However, it is contemplated that one or more steps of method 300 may be accomplished via means alternative to those described by the foregoing embodiments of the PMT 100. Accordingly, method 300 is intended to encompass any means known to the art for carrying out the steps that follow.

In steps 302 to 306 a typical construction of a PMT 100 is provided, including a photocathode 102, a plurality of dynodes 104 disposed within a multiplier tube 101, and an anode 106. As described above, the photocathode 102 may emit electrons in response to incident illumination. The electrons are then accelerated through the multiplier tube 101 and multiplied via secondary emissions by the dynodes 104. The multiplied electrons are received by the anode 106 resulting in a sudden rise of detected current from the PMT 100. At step 308 a weakly repulsive electric field is introduced via a control grid 108 or any functional equivalent known to the art. The repulsive field prevents low-energy electrons emitted by the photocathode 102 from being accelerated through the multiplier tube 101 by the dynodes 104 to the anode 106. Low-energy electrons, which may be emitted as a result of thermal excitation after illumination no longer impinges upon the photocathode 102, are accordingly prevented from affecting the current detected from the PMT 100. As a result, intensity peaks due to incident illumination are followed by a rapid decay of current allowing for extended dynamic range.

Method 300 may further include one or more steps for carrying out a function described with regard to foregoing embodiments of system 100 or system 200. As such, the foregoing steps are illustrative of an embodiment of the method and should not be construed as limitations. Those having skill in the art will further appreciate that there are various vehicles by which processes, systems and/or other technologies described herein can be effected (e.g. various combinations of hardware, software, and/or firmware). The preferred vehicle will vary with the context of implementation.

Program instructions implementing steps or functions, such as those described herein, may be transmitted over or stored on carrier media. In some embodiments, a carrier medium may include a transmission medium such as a wire, cable, or wireless transmission link. In some embodiments, the carrier medium may include a storage medium such as a read-only memory, a random access memory, a magnetic or optical disk, or a magnetic tape.

Some of the steps or functions described herein require storage of results by a storage medium. The results may include any collected or determined information described herein and may be stored in any manner known in the art. After the results have been stored, the results may be accessed from the storage medium and utilized for any of the methods or system embodiments described herein, formatted for display to a user, used by another software module, method, or system, etc. Furthermore, the results may be stored permanently, semi-permanently, or temporarily (i.e. for a specified or indefinite period of time). For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. A photomultiplier tube, comprising:
   a photocathode configured to emit electrons in response to incident illumination;

a plurality of dynodes configured to multiply electrons received from the photocathode;

an anode configured to receive electrons multiplied by the plurality of dynodes; and a control grid configured to maintain an electric potential sufficient to block at least some thermal electrons emitted by the photocathode, following illumination of the photocathode with the incident illumination, from being received by the plurality of dynodes to enhance dynamic range of the photomultiplier tube.

2. The photomultiplier tube of claim 1, wherein the control grid is disposed between the photocathode and a first dynode of the plurality of dynodes.

3. The photomultiplier tube of claim 2, wherein the control grid is arranged substantially parallel to the photocathode.

4. The photomultiplier tube of claim 2, further comprising:
an accelerating grid disposed between the control grid and the first dynode.

5. The photomultiplier tube of claim 1, wherein the control grid includes a conductor configured to maintain a negative electric potential relative to an electric potential of the photocathode.

6. The photomultiplier tube of claim 5, wherein the conductor includes a wire mesh.

7. The photomultiplier tube of claim 5, wherein the conductor is configured to maintain an electric potential in the range of approximately −0.5 V to −1 V relative to the electric potential of the photocathode.

8. The photomultiplier tube of claim 1, wherein the electric potential maintained by the control grid is sufficiently small to transmit at least some primary electrons emitted by the photocathode to the plurality of dynodes.

9. The photomultiplier tube of claim 1, wherein the electric potential maintained by the control grid is a constant electric potential.

10. An inspection system, comprising:
at least one illumination source configured to illuminate a sample;
at least one detector configured to receive illumination scattered, reflected, or radiated from the sample, the at least one detector comprising a photomultiplier tube including:
a photocathode configured to emit electrons in response to the illumination received from the sample,
a plurality of dynodes configured to multiply electrons received from the photocathode,
an anode configured to receive electrons multiplied by the plurality of dynodes, and
a control grid configured to maintain an electric potential sufficient to block at least some thermal electrons emitted by the photocathode, following illumination of the photocathode with the incident illumination, from being received by the plurality of dynodes to enhance dynamic range of the photomultiplier tube; and
at least one computing system in communication with the at least one detector, the at least one computing system configured to determine information associated with at least one defect of the sample based upon the illumination received by the at least one detector from the sample.

11. The inspection system of claim 10, wherein the control grid is disposed between the photocathode and a first dynode of the plurality of dynodes.

12. The inspection system of claim 11, wherein the control grid is arranged substantially parallel to the photocathode.

13. The inspection system of claim 10, wherein the photomultiplier tube further includes:
an accelerating grid disposed between the control grid and the first dynode.

14. The inspection system of claim 10, wherein the control grid includes a conductor configured to maintain a negative electric potential relative to an electric potential of the photocathode.

15. The inspection system of claim 14, wherein the conductor includes a wire mesh.

16. The inspection system of claim 14, wherein the conductor is configured to maintain an electric potential in the range of approximately −0.5 V to −1 V relative to the electric potential of the photocathode.

17. The inspection system of claim 10, wherein the inspection system is configured for darkfield inspection.

18. The inspection system of claim 10, wherein the electric potential maintained by the control grid is sufficient to block at least some electrons emitted by the photocathode via thermal excitation of surface states of the photocathode from being received by the plurality of dynodes.

19. The inspection system of claim 10, wherein the electric potential maintained by the control grid is sufficiently small to transmit at least some primary electrons emitted by the photocathode to the plurality of dynodes.

20. The inspection system of claim 10, wherein the electric potential maintained by the control grid is a constant electric potential.

21. A method of extending dynamic range of a photomultiplier tube, comprising:
providing a photocathode configured to emit electrons in response to incident illumination;
providing a plurality of dynodes configured to multiply electrons received from the photocathode;
providing an anode configured to receive electrons multiplied by the plurality of dynodes; and
introducing a repulsive constant electric field to prevent a portion of thermal electrons emitted by the photocathode, following illumination of the photocathode with the incident illumination, from being received by the plurality of dynodes.

22. The method of claim 21, wherein the introducing the repulsive electric field includes:
disposing a control grid between the photocathode and a first dynode of the plurality of dynodes; and
applying an electric potential to a conductor of the control grid, the electric potential being negative relative to an electric potential of the photocathode.

23. The method of claim 22, further comprising:
disposing an accelerating grid between the control grid and the first dynode.

24. The method of claim 22, wherein the conductor includes a wire mesh.

25. The method of claim 22, wherein the electric potential applied to the conductor is in the range of approximately −0.5 V to −1 V relative to the electric potential of the photocathode.

* * * * *